United States Patent
Doré et al.

(10) Patent No.: US 7,636,459 B2
(45) Date of Patent: Dec. 22, 2009

(54) HIGH PRECISION MODELING OF A BODY PART USING A 3D IMAGING SYSTEM

(75) Inventors: Sylvie Doré, Montreal (CA); Yves Goussard, Montreal (CA); Jérôme Idier, Nantes (FR); Nicolas Villain, Clamart (FR)

(73) Assignees: Centre National de la Recherche Scientifique (C.N.R.S.), Paris (FR); Ecole De Technologie Superieure, Montreal (CA); Polyvalor, S.E.C., Montreal (CA)

( * ) Notice: Subject to any disclaimer, the term of this patent is extended or adjusted under 35 U.S.C. 154(b) by 601 days.

(21) Appl. No.: 10/425,989

(22) Filed: Apr. 30, 2003

(65) Prior Publication Data

US 2003/0236473 A1 Dec. 25, 2003

Related U.S. Application Data

(63) Continuation of application No. PCT/CA01/01541, filed on Oct. 31, 2001.

(60) Provisional application No. 60/244,175, filed on Oct. 31, 2000.

(51) Int. Cl.
*G06K 9/00* (2006.01)
(52) U.S. Cl. .................. 382/128; 623/18.11; 623/16.11
(58) Field of Classification Search .................. 600/407, 600/408; 128/898, 922; 382/128; 623/18.11, 623/16.11
See application file for complete search history.

(56) References Cited

U.S. PATENT DOCUMENTS

| | | | |
|---|---|---|---|
| 4,436,684 A | 3/1984 | White | |
| 4,841,975 A | 6/1989 | Woolson | |
| 4,936,862 A | 6/1990 | Walker et al. | |
| 4,976,737 A | 12/1990 | Leake | |
| 5,007,936 A | 4/1991 | Woolson | |
| 5,037,442 A | 8/1991 | Wintermantel et al. | |
| 5,047,057 A | 9/1991 | Lawes | |
| 5,150,304 A | 9/1992 | Berchem et al. | |
| 5,326,367 A | 7/1994 | Robioneck | |
| 5,360,446 A | 11/1994 | Kennedy | |
| 5,370,692 A | 12/1994 | Fink et al. | |
| 5,516,532 A | 5/1996 | Atala et al. | |
| 5,554,190 A | 9/1996 | Draenert | |

(Continued)

OTHER PUBLICATIONS

Parrot et al. Towards Statistically Optimal Interpolation for 3D Medical Imaging. Engineering in Medicine and Biology Magazine, IEEE, 1993 vol. 12(3). 49-59.*

(Continued)

*Primary Examiner*—Long V Le
*Assistant Examiner*—Sanjay Cattungal
(74) *Attorney, Agent, or Firm*—Birch, Stewart, Kolasch & Birch, LLP (57) ABSTRACT

A method and apparatus is disclosed for modeling a body part with a high precision. Image data of a body part is collected from an imaging system with a first resolution. After processing the image data collected from the imaging system, a 3-dimensional description of the body part is generated, the 3-dimensional description of the body part having a second resolution higher than the first one. A 3-dimensional parametric description of the body part is then generated. The 3-dimensional parametric description may be used to create a replica of the body part or an implant tightly fitting the said body part.

20 Claims, 3 Drawing Sheets

U.S. PATENT DOCUMENTS

| | | | |
|---|---|---|---|
| 5,571,203 | A | 11/1996 | Masini |
| 5,636,255 | A | 6/1997 | Ellis |
| 5,681,354 | A | 10/1997 | Eckhoff |
| 5,682,886 | A | 11/1997 | Delp et al. |
| 5,735,277 | A | 4/1998 | Schuster |
| 5,741,215 | A | 4/1998 | D'Urso |
| 5,768,134 | A | 6/1998 | Swaelens et al. |
| 5,769,092 | A | 6/1998 | Williamson, Jr. |
| 5,824,083 | A | 10/1998 | Draenert |
| 5,824,085 | A | 10/1998 | Sahay et al. |
| 5,871,018 | A | 2/1999 | Delp et al. |
| 5,880,976 | A | 3/1999 | DiGioia III et al. |
| 5,951,475 | A | 9/1999 | Gueziec et al. |
| 5,995,738 | A * | 11/1999 | DiGioia et al. ............... 703/11 |
| 6,067,340 | A | 5/2000 | Eppstein et al. |
| 6,112,109 | A | 8/2000 | D'Urso |

OTHER PUBLICATIONS

Villain et al. Proceedings—19th International Conference—IEEE/EMBS Oct. 30-Nov. 2, 1997 Chicago, IL. USA. 561-564.*

Image Restoration in Computed Tomography: The Spatially Invariant Point of Spread Function, Satyapal Rathee et al, IEEE 1992 Transactions on Medical Imaging, vol. 11, No. 4, Dec. 1992, pp. 530-538.

Unsupervised 3-D Restoration of Tomographic Images by Constrained Wiener Filtering, Shelby Pereira et al.Proceedings—19$^{th}$ International Conference IEEE /EMBS Oct. 30-Nov. 2, 1997, Chicago, IL pp. 557-560.

Influence of CT Scanner Characteristics on 3D Reconstruction Accuracy, S. Doré et al., C MBEC—15—CCGB, Toronto 1989, pp. 26-27.

Variability of CT Point Spread Function within the Field of View, S. Doré et al., Annual International Conference of the IEEE Engineering in Medicine and Biology Society, vol. 12, No. 1, 1990, pp. 0242-0243.

Unique Orthopedic Implants, S. Doré et al., SOMA/Apr. 1986, pp. 45-53.

Optimized Single Site Update Algorithms for Image Deblurring, Stéphane Brette et al., Lab. Des Signayx et Systèmes (CNRS/ESE/UPS, 4 pages.

Experimental Determination of CT Point Spread Function Anisotropy and Shift-Variance, S. Doré et al., Proceedings—19$^{th}$ International IEEE 1997, pp. 788-791.

Quantitative Assessment of CT PSF Isotropicity and Isoplanicity, S. Doré et al., Winnipeg, Canada 1990, pp. 33 and 32.

Approche Régularisée en Reconstruction tomographique 3D Hélicoidale, Marc Allain et al. -4 pages.

Restauration par champs de Markov 3D à Potentiels Convexes appliquée aux images tomographiques, Nicolas Villain et al., 17th Coloque GRETSI, Vannes Sept. 13-17, 1999, pp. 599-602.

Image Restoration in Computed Tomography, Restoration of Experimental CT Images, Satyapal Rathee et al., IEEE Transactions on Medical Imaging, vol. 11, N° 4, Dec. 1992, pp. 546-553.

* cited by examiner

HIGH PRECISION MODELING OF A BODY PART USING A 3D IMAGING SYSTEM

CROSS-REFERENCE TO RELATED APPLICATIONS

This patent application is a continuation of PCT patent application No. PCT/CA01/01541 that designates the U.S. and was filed Oct. 31, 2001 and which claims priority of U.S. provisional patent application No. 60/244,175 that was filed Oct. 31, 2000.

TECHNICAL FIELD

The invention concerns a method of reverse engineering the geometry of a part of human or animal anatomy with emphasis on high precision modeling of critical surfaces and methods leading to the fabrication of mating prosthetic elements adapted to the aforementioned anatomical surfaces.

BACKGROUND OF THE INVENTION

It is common practice to replace a severely ailing joint with an endoprosthesis. With current commercially available models, surgeons must remove a considerable amount of bone in order to put the implant in place. This compromises bone stock for future implant revision in the advent of implant failure and is one of the major reasons why such operations are rarely performed on young patients. This problem could be alleviated by the use of thin resurfacing implants. Especially when used in highly loaded joints, such implants are subject to bending stresses which can lead to fatigue fracture if they are not properly supported. Ideally, the implant should be placed over hard cortical bone, not cancellous bone as is current practice. This implies that no bone should be removed at the moment of the operation, thereby guaranteeing a healthy bone stock for eventual revision, but at the expense of a high precision customization of the shape of the implant to the particular geometry of the articulating surface of the afflicted joint of each patient.

Since the advent of digital tomographic medical imaging, research teams around the world have strived to generate three-dimensional computer—or numerical—models in order to improve visualization of internal anatomy. Generically, obtaining digitized geometric data from an object and creating a numerical model of said object from the digitized data is often referred to as geometric reverse engineering. Combined with numerically controlled fabrication technologies, whether they be more traditional machines based on removal of material such as numerically controlled (N/C) milling or turning, or on more recent methods based on addition of material on a slice by slice basis—methods known as rapid prototyping, free-form fabrication or other names—it is possible to create a physical, as opposed to numerical, model of internal structures. These physical models can be used for diagnostic purposes or for surgery planning and rehearsal. They can also be used as templates from which a prosthetic element can be fashioned. By manipulating the numerical model, it is also possible to directly fabricate prosthetic elements adapted to the geometry of internal structures.

Conventionally, the method used to reproduce the portion of the body, or for which an implant is to be fabricated, can be described as follows. The body part under investigation is imaged with a medical imaging apparatus. This can be laser or acoustic reflection based apparatus or a number of transmission apparatus such as standard X-ray radiographs, planar or spiral X-ray computer tomography, magnetic resonance imaging, positron emission tomography, magnetic resonance angiography, etc. The images produced are analyzed with readily available image processing techniques such as thresholding, which consists of segmenting or isolating regions on the basis of grey values, mathematical morphology operations such as reduction, expansion, dilatation, etc. and Boolean operations. Once the contours of the desired anatomical structure or structures are identified within each image, a three-dimensional model is generated by interpolating data. This is usually done by using creating a mesh of triangular facets. This method offers many advantages: it is quickly computed, it can be rapidly visualized and manipulated numerically in order to rotate, translate, scale and perform other operations, it is perfectly adapted to the "de facto" standard STL file format used by all rapid prototyping machines. Instead of creating a mesh of triangular facets, one can exploit higher order interpolation functions implemented in CAD systems. These systems can then generate an STL file for fabrication with a rapid prototyping apparatus, with a loss of precision in the process, or G code if fabrication with more traditional material cutting or removal technologies is envisioned.

The method previously described strives to produce as exact a copy as possible of the anatomy under consideration. However, the original data produced by the imaging apparatus is tainted by distortions introduced by the imaging modality. For example, the precision with which the edges of structures can be located is limited by the imaging resolution, or blur, of the apparatus and by imprecision—or noise—introduced by the imaging apparatus. In the methods proposed to this day, knowledge of the distortions has never been exploited in order to improve the original data prior to image analysis. Furthermore, the creation of the three-dimensional model, and the subsequent data generated to drive an N/C fabrication machine can also contribute to further loss of information. Because N/C machines are much more precise than the data obtained by medical imaging modalities, it is common practice to interpolate data. Typically, this consists of interpolating intermediate "slices" between the slices corresponding to the tomographic images. For example, if a rapid prototyping machine can build a layer of 0.25 mm but that the imaging apparatus generates images of structures 1 mm in thickness, then the geometry of three additional layers must be interpolated between two consecutive image layers. The additional layers can be simple repetitions of one of the original image layer, which corresponds to zero order interpolation. A more popular approach, that of generating a triangular mesh and then "slicing" this mesh to the desired machine accuracy, corresponds to first order interpolation. In both situations, discontinuities appear in the model. If one strives for accuracy, higher order interpolation techniques must be used and care must be taken to insure coherent data representation at all stages. It would be useless to use a third degree interpolation scheme, as a NURBS representation implemented in a CAD system for example, if it is later converted into an STL file for fabrication on a rapid prototyping machine, the STL file corresponding to first order interpolation.

When rapid prototyping technologies are used to fabricate the physical model, it is common practice to position the part to be built in the same orientation within the rapid prototyping machine as the patient within the imaging scanner. Therefore, material is added in a slice orientation parallel to the images produced by the imaging apparatus. U.S. Pat. No. 5,741,215 suggests a method for reducing the time, and therefore the cost, required to make a physical model by stereolithography through selective orientation of the model. The author of the patent also claims that the method can be used to fabricate an implant shaped to correct an anatomical defect, implant characterized in having a close fit with connective tissue and contours appropriate for an implant site. Presumably, selective orientation of the model can improve the fit but there is neither mention of improving image data nor of coherent data representation. Furthermore, the proposed application is quite different than having a close fit over the whole surface of the implant in order to insure proper mating with underlying bone.

U.S. Pat. Nos. 5,554,190 and 5,824,083 propose a method based on CAD and image-analysis methods for producing an anchored prosthetic component which provides the largest possible surface for transmission of forces, and its mass and rigidity can be adapted to the individual properties of the bone. Contrarily to resurfacing implants where the loads are principally transmitted perpendicularly to the implant, loads are transmitted parallel to the anchored element, creating very different requirements on design and precision for both applications. Here again, no mention of data improvement nor of data coherency can be found.

In U.S. Pat. No. 5,768,134, the authors set out not only to reproduce the geometry of an anatomical structure but to make a perfected model characterized by at least one artificial functional element with a useful function added to the basic anatomical model. This artificial functional element is created on the basis of the grey value data image information and possibly of additional external information. The external information is provided by the medical user. In order to improve the fit, the authors suggest interpolating contours with sub-pixel accuracy. However, it does not make use of the information on the degradation induced by the imaging modality in order to improve the quality of the images prior to using the image information. Furthermore, as with other proposed methods, there is no particular attention to the three-dimensional representation of the anatomical surface insuring a minimum loss of information.

None of the prior methods or applications addresses the problems posed by the necessity of high precision modeling of critical anatomical surfaces and particularly of methods leading to the fabrication of a mating prosthetic element adapted to the aforementioned anatomical surfaces whereby loads are transmitted in a direction perpendicular to the prosthetic element.

SUMMARY OF THE INVENTION

Accordingly, an object of the present invention is to provide a method for modeling a body part using information collected by an imaging system.

Another object of the present invention is to provide a method for modeling a body part using information collected by an imaging system, with a precision higher than the precision provided by the imaging system, allowing a user to reproduce the body part or an implant tightly fitting the said body part using a manufacturing tool.

Another object of the present invention is to provide a method for modeling a body part using information collected by an imaging system, with a precision higher than the precision provided by the imaging system, allowing a user to reproduce the body part or an implant tightly fitting the said body part using a manufacturing tool after a manipulation using a CAD system.

In accordance with a first aspect of the invention, there is provided a method for high precision modeling of a body part, the method comprising the steps of collecting image data of a body part provided by an imaging system with a first imaging resolution, processing the collected image data of the body part using data representing the imaging behavior of the imaging system and information about the nature of the body part to provide a 3-dimensional description data of the body part, the 3-dimensional description data of the body part having an image resolution better than the first imaging resolution and processing the 3-dimensional description data of the body part to provide a 3-dimensional parametric description of the body part.

According to another aspect of the invention, there is provided an apparatus for generating a 3-dimensional parametric description of a body part, the apparatus comprising an imaging system providing a data image signal of the body part, a processing unit receiving the data image signal of the body part with a first imaging resolution, the processing unit further receiving data representing the imaging behavior of the imaging system and information about the nature of the body part, the processing unit providing a 3-dimensional description data of the body part and a 3-dimensional parametric description generator unit, receiving the 3-dimensional description data of the body part and providing a 3-dimensional parametric description of the body part, the 3-dimensional description data of the body part having an image resolution higher than the first imaging resolution.

According to another aspect of the invention, there is provided An apparatus for manufacturing an implant, the apparatus comprising an imaging system providing a data image signal of the body part, a processing unit receiving the data image signal of the body part with a first imaging resolution, the processing unit further receiving data representing the imaging behavior of the imaging system and information about the nature of the body part, the processing unit providing a 3-dimensional description data of the body part, a 3-dimensional parametric description generator unit, receiving the 3-dimensional description data of the body part and providing a 3-dimensional parametric description of the body part, the 3-dimensional description data of the body part having an imaging resolution higher than the first imaging resolution and a manufacturing unit, receiving the 3-dimensional parametric description data of the body part from the 3-dimensional parametric description generator unit and manufacturing the body part.

Preferably, the body part is a surface, such as a bone-cartilage interface.

Preferably, the 3D parametric description is selected to be suitable for the body part. Also preferably, the 3D parametric description is suitable for input to a N/C machine tool or rapid prototyping apparatus leading to the manufacture of a resurfacing articular prosthetic element.

The 3D imaging system may be any imaging modality providing information on the 3D geometry of the part of the anatomy under investigation, such as X-ray tomography, MRI, Spect, PET etc. The image data may be in the form of raw data (projection data) or in the form of a series of reconstructed images. The information processing method transforms the image data provided by the imaging system into an enhanced and precise 3D voxel-based description of the part of the anatomy under investigation. It makes use of specific information about the imperfections of the image data provided by the imaging system, and about the nature of the part of the anatomy under investigation, e.g., presence of quasi-homogeneous areas separated by sharp discontinuities. The result provided by the information processing method is suitable for precise determination of the position of any number of points located on landmarks or areas of interest of the part of the anatomy under investigation by fast and simple means such as thresholding with an accuracy greater than that of the imaging apparatus (optical resolution and precision of the built-in reconstruction algorithm).

The geometric modeling technique transforms the 3D voxel-based image of the part of the anatomy under investigation into a numerical description suitable for N/C fabrication of a precise replica of the part of the anatomy or of an implant tightly fitting the said part of the body. Because the accuracy of N/C machines is much greater than the distance separating data obtained by medical imaging modalities, the density of data must be increased prior to fabrication. This is done by representing the surface (boundaries) of the part of the anatomy under investigation with a global 3D parametric model that can provide a numerical description with arbitrary density in order to adapt to requirements of different types of N/C fabrication methods (e.g., machining, rapid prototyping, etc.). This description is directly derived from the parametric model and can be provided in several geometric orientations and various formats (e.g., STL, SLC, G-code) without conversion so as to adapt to different types of N/C fabrication methods without loss of precision.

The method can be used in numerous applications. One example of such applications is the fabrication of personalized resurfacing knee implants. Such implants are heavily loaded in a direction perpendicular to the prosthetic element and therefore, the inner surface of the implant must mate precisely with the underlying bone in order to ensure adequate functionality and durability. A series of two-dimensional (2D) images of the knee can be obtained from a planar or spiral X-ray tomograph. Such images present distortion and artifacts of a magnitude that precludes their direct use for fabrication of the implant. However, the series of images can be processed with a 3D restoration method that accounts for the nature of the distortion and of the artifacts, and that accounts for the nature of the body part by means of a statistical 3D Markov random field model. Then, a global 3D parametric model of the distal femur can be derived from the restored images using Kriging techniques. This allows direct extraction of arbitrarily spaced contours (SLC format) so as to build a replica of the distal femur with a rapid prototyping technique. The replica can then be used as a template for fabricating the personalized resurfacing implant through casting techniques. A tight fit between implant and distal femur is possible due to the synergy between the 3D image restoration method and the Kriging-based parametric modeling of the distal femur.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION OF THE PREFERRED EMBODIMENT

Figure 1:
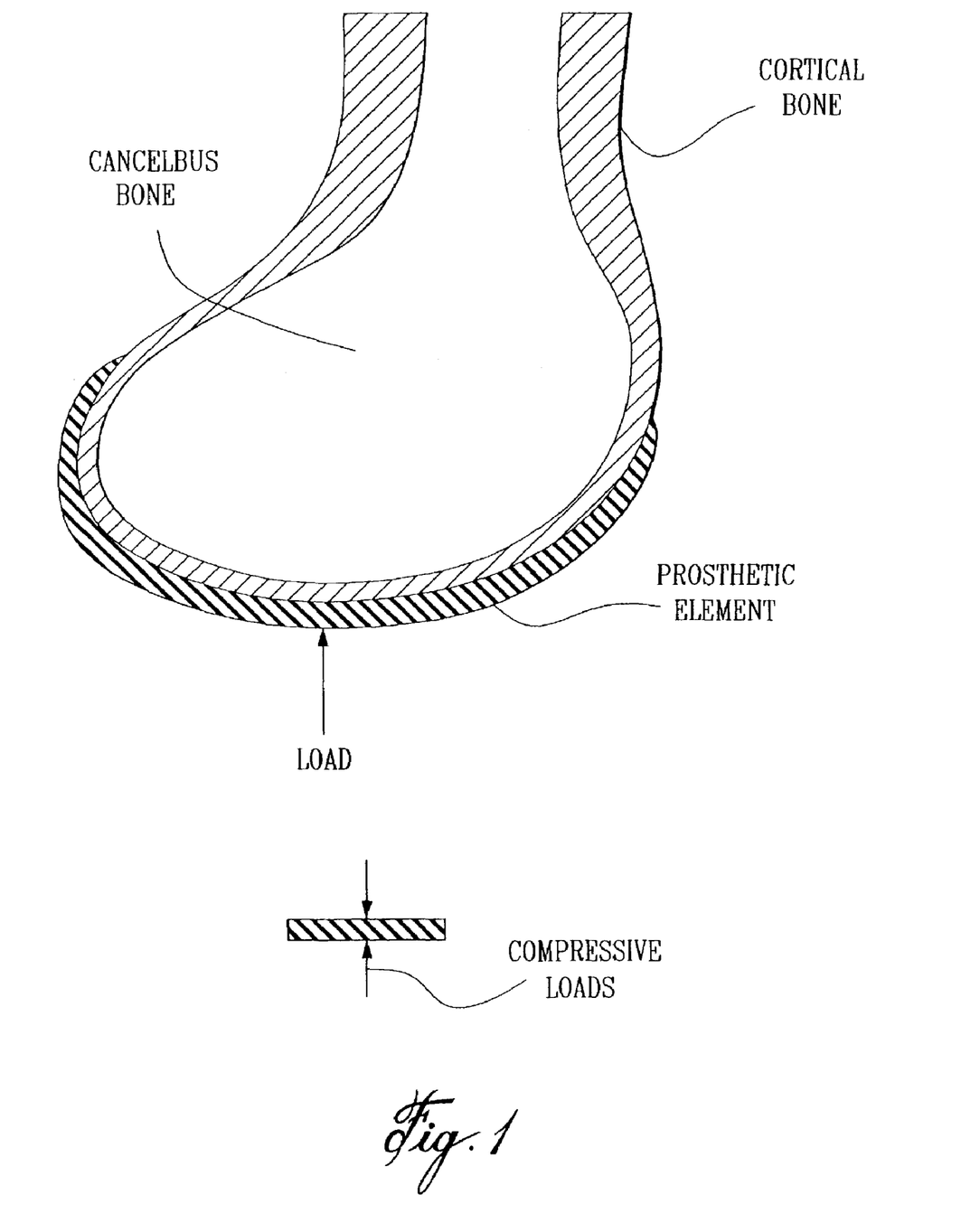
FIG. 1 shows a perfectly fitted resurfacing articular implant.
Figure 2:
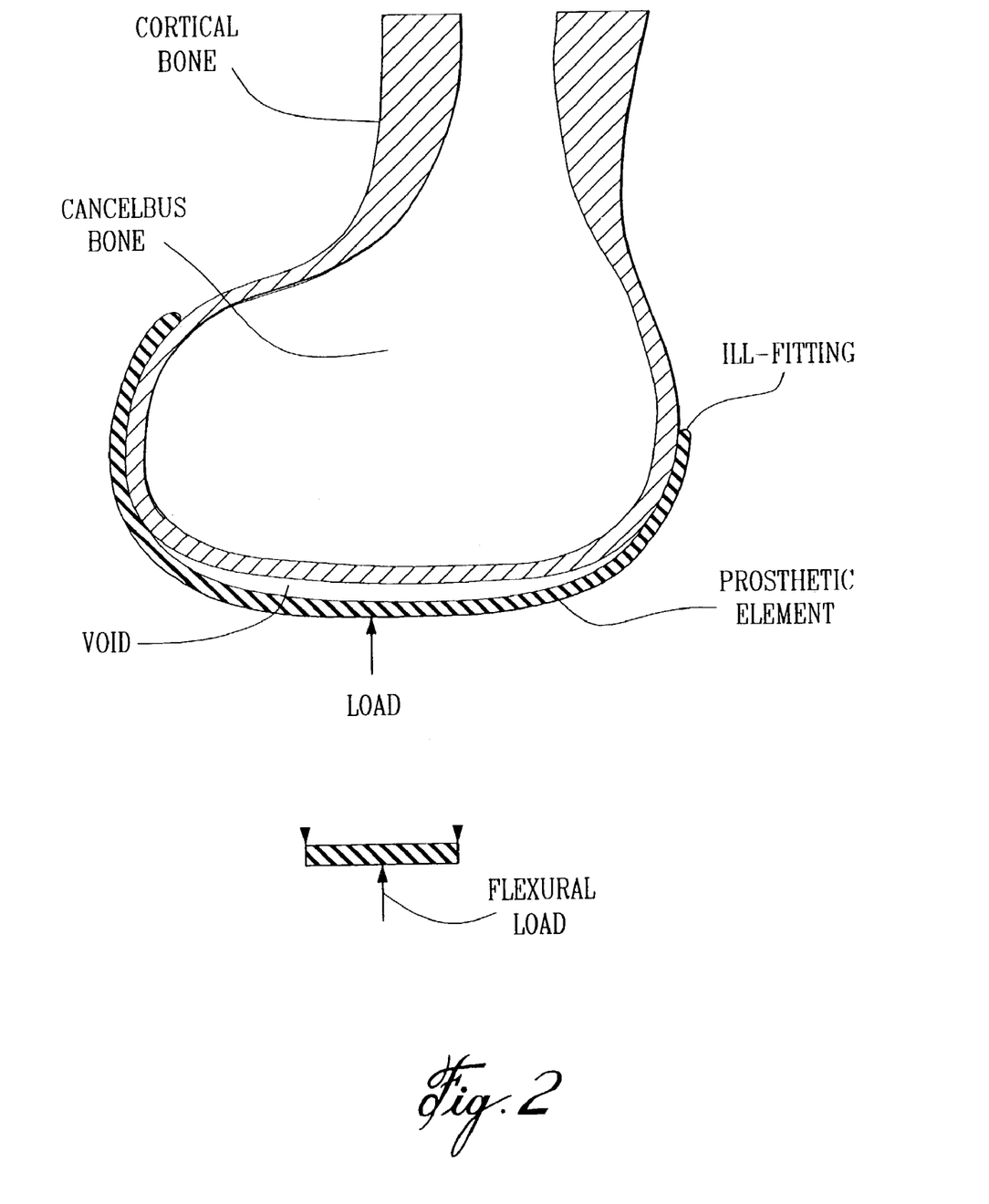
FIG. 2 shows an imperfectly fitted resurfacing articular implant.

An ideal articular resurfacing implant, as depicted in FIG. 1, mates perfectly with the articular surface, thus insuring that loads are principally compressive in nature. If the implant is not well supported, as shown in FIG. 2, bending loads which can eventually lead to fatigue fracture are generated. Ideally, the implant should sit on cortical bone and its thickness should match that of the cartilage which it replaces. The implant is composed of a biocompatible material, whether metallic, polymeric or ceramic. It can also be a composite, a metal base covered by a polymer for example. Fixation of the implant can be insured through bioactivity, osteointegration, or an anchoring device such as a screw. If the shape of the implant is sufficiently enfolding, mechanical fit will be sufficient to keep it in place.

Figure 3:
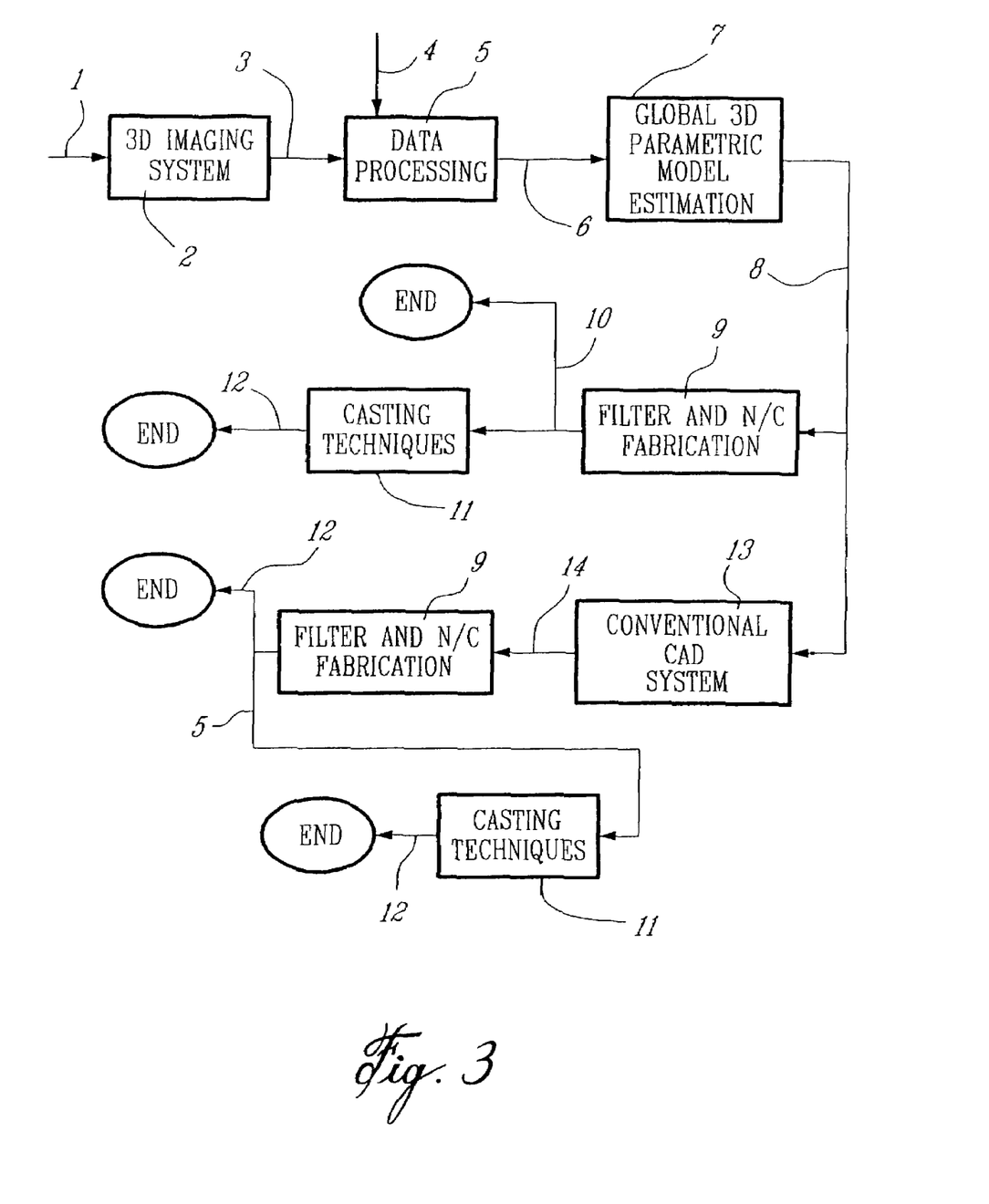
FIG. 3 shows a flow chart from data collection to fabrication of a physical model or prosthetic element.

FIG. 3 depicts a method of producing such an implant with the accuracy required by this application. First, in order to obtain geometric information about the body part under investigation 1, image data are collected using a 3D imaging system 2. The imaging system may be an X-ray planar or spiral tomograph, a MRI device, a SPECT device, a PET device etc. The imaging behavior is related to the imperfections, distortions or spatial transformations in the image of the object. In the preferred embodiment, the imaging behavior is characterized by the Point Spread Function. The image data 3 may be in raw form (projection data) or in reconstructed form (series of images). The amount of the image data collected at this stage as well as the orientation of the body part in the imaging apparatus must be planned carefully in order to optimize trade-off between the quality of the geometric information and the patient well-being and comfort (radiation doses, position). However, the optical resolution of the imaging apparatus and the precision of the built-in image reconstruction software are below the precision required for fabrication of the implant.

In order to improve the quality of the geometric information, the image data undergoes an information-processing step 5 which makes use of specific information about the imperfections of the image data provided by the imaging system, and about the nature of the part of the anatomy under investigation 4. If the image data are in reconstructed form, this information can be introduced as a linear degradation model (point spread function (PSF)) with addition of random errors. Both the PSF and the statistics of the random errors must be assessed beforehand. If the images data are in raw form, the information are introduced as geometric parameters of the imaging system and as random errors, which both must be assessed beforehand. The information about the nature of the part of the anatomy under investigation is introduced in the form of a 3D statistical model designed to capture salient features of the said part. If such a feature is a general smoothness, 3D Gaussian models may be appropriate. If such a feature is the presence of quasi-homogeneous areas separated by sharp discontinuities 3D non-Gaussian Markov random field (MRF) models may be used. The information about the imaging apparatus and the body part are combined into a single information processing method 5, which falls in the category of 3D restoration if the image data are in image form and a 3D reconstruction if the data are in raw form. The information-processing step 5 provides results in the form of a 3D voxel-based image 6. Because the accuracy is now greater than that of the imaging apparatus 2 (optical resolution and precision of the built-in reconstruction algorithm), the 3D voxel-based image is suitable for precise determination of the position of a large number of points located on landmarks or areas of interest of the part of the anatomy under investigation by fast and simple means such as thresholding.

In order to fabricate a precise replica of the part of the anatomy under investigation or of an implant tightly fitting the said part, its shape must be specified in a computer file in an appropriate format (G-code for conventional N/C milling machines, STL or SLC for rapid prototyping machines). The computer file contains the coordinates of points located on the surface of the part to be fabricated. The density of these points must be higher than that of the 3D image 6 because the accuracy of N/C machines is much greater than the resolution of medical imaging apparatus.

In order to generate surface points with arbitrary density, a global 3D parametric model of the surface (boundaries) of the part of the anatomy under investigation is estimated in step 7. In one embodiment of the invention, a Kriging technique can be used. This step also requires the selection of a reference system adapted to the shape under investigation and of the number of parameters required by the desired precision. Once these selections are made, the parameter values must be determined from the 3D voxel-based image 6 using an appropriate technique. Typically, this is accomplished by selecting an appropriate number of points in the 3D image 6 located on the surface to be modeled and by applying a linear estimation method for estimation of the parameters of the global 3D model. This results in the parametric description 8 of the whole surface of the body part under investigation 1.

The parametric description 8 can be utilized in a number of ways, two of which are described here. Firstly, it can provide the coordinates of any number of points located on the surface of the modeled body part. Therefore, it can yield data for N/C fabrication of a replica of the body part under investigation 10 in any appropriate format through the simple filtering operation 9. The replica can then be used directly for surgery planning for example, or as an intermediate tool for conventional fabrication of the prosthetic element 12 using casting techniques 11. Secondly, the model can be manipulated using a conventional CAD system 13 in order to obtain a model of the positive or of the negative of the body part 14. The model 14 can then be utilized either for direct N/C fabrication of the prosthetic element 12 after a simple filtering operation 9 or for producing a positive or negative replica of the prosthetic element 15 from which the prosthetic element 12 is fabricated by means of standard casting techniques 12.

A particular embodiment of the method is the fabrication of personalized resurfacing knee implants in the following manner: a series of appropriately spaced 2D images of the knee joint are obtained from a spiral X-ray tomograph, thereby producing the data set 3 which is here in reconstructed form.

The magnitude of the distortions, the artifacts and the noise present in the data set preclude its direct use for fabrication of the implant. However, the nature of these distortions, artifacts and noise can be modeled by a noise-corrupted space-invariant linear degradation whose precise characteristics can be identified beforehand. In addition, the part of the body under study 1—the knee joint—is made up of quasi homogeneous organs (the bone tissues, the soft tissues etc.) separated by sharp transitions and non Gaussian MRFs are appropriate statistical models of the 3D image of the knee. These two sources of information can be combined in order to yield a 3D MRF image restoration method which constitutes the information-processing step 5. The result of the 3D restoration is the 3D voxel-based image 6 whose precision is now greater than that of the spiral X-ray tomograph and which is suitable for accurate determination of the coordinates of a large number of points located on or near the surface of the cortical bone of the distal femur. An appropriate number of such points—referred to as control points are selected in order to estimate a parametric model of the bone surface in step 7. A cylindrical coordinate system is chosen because it is well adapted to the general shape of the distal femur.

The model parameters are determined from the control points using a Kriging technique. The parametric description of the distal femur 8 is then used to produce a replica 10 by means of a rapid prototyping technique. This requires to choose a format for control of the fabrication operation. In order to minimize the errors generated by conversion operations, the SLC format is selected because it is in direct correspondence with the slice-by-slice fabrication process that rapid prototyping 9 is based upon. In addition, the parametric model can yield a SLC file with arbitrary density along several directions, thereby allowing for added flexibility.

The fabricated replica of the distal femur 10 is then used for manual design and fabrication of the prosthetic element 12 using conventional casting techniques 11.

The embodiments of the invention described above are intended to be exemplary only. The scope of the invention is therefore intended to be limited solely by the scope of the appended claims.

We claim:

1. A method for high precision modeling of a body part, the method comprising the steps of:
   collecting image data of a body part provided by an imaging system with a first spatial resolution;
   processing the collected image data of the body part using data representing the imaging behavior of the imaging system and information about the nature of the body part to provide a 3-dimensional description data of the body part, the 3-dimensional description data of the body part having an spatial resolution better than the first spatial resolution; and
   processing the 3-dimensional description data of the body part to provide a 3-dimensional parametric description of the body part.

2. The method as claimed in claim 1, wherein the 3-dimensional description data of the body part is voxel-based.

3. The method as claimed in claim 1, wherein the collected image data provided by the imaging system are in raw form.

4. The method as claimed in claim 1, wherein the collected image data provided by the imaging system are in reconstructed form.

5. The method as claimed in claim 3, wherein the imaging behavior of the imaging system is defined using geometric parameters of the imaging system with addition of random errors.

6. The method as claimed in claim 4, wherein the imaging behavior of the imaging system is defined using a linear degradation model (point spread function) with addition of random errors.

7. The method as claimed in claim 1, wherein the information about the nature of the body part is introduced using a 3-D statistical model of the body part.

8. The method as claimed in claim 1, wherein the step of processing the 3-dimensional description data of the body part to provide a 3-dimensional parametric description of the body part is performed using a Kriging technique.

9. The method as claimed in claim 1, further comprising the step of building the body part using the 3-dimensional parametric description of the body part.

10. The method as claimed in claim 9, wherein the step of building the body part using the 3-dimensional parametric description of the body part comprises the step of filtering the 3-dimensional parametric description of the body part.

11. An apparatus for generating a 3-dimensional parametric description of a body part, the apparatus comprising:
    an imaging system providing a data image signal of the body part;
    a processing unit configured to reveive the data image signal of the body part with a first spatial resolution, the processing unit further configured to reveive data representing the imaging behavior of the imaging system and information about the nature of the body part, the processing unit configured to provided a 3-dimensional description data of the body part; and a 3-dimensional parametric description generator unit, receiving the 3-dimensional description data of the body part and providing a 3-dimensional parametric description of the body part, wherein the 3-dimensional description data of the body part having an spatial resolution higher than the first spatial resolution.

12. An apparatus for manufacturing an implant, the apparatus comprising:

an imaging system providing a data image signal of the body part;

a processing unit configured to reveive the data image signal of the body part with a first spatial resolution, the processing unit further configured to reveive data representing the imaging behavior of the imaging system and information about the nature of the body part, the processing unit configured to provided a 3-dimensional description data of the body part;

a 3-dimensional parametric description generator unit, receiving the 3-dimensional description data of the body part and providing a 3-dimensional parametric description of the body part, wherein the 3-dimensional description data of the body part having an spatial resolution higher than the first spatial resolution; and a manufacturing unit, receiving the 3-dimensional parametric description data of the body part from the 3-dimensional parametric description generator unit and manufacturing the body part.

13. The apparatus as claimed in claim 12, for the fabrication of a personalized resurfacing knee implant, the processing unit receiving 2D images of the knee joint from an X-ray tomograph.

14. The apparatus as claimed in claim 11, wherein the imaging system is a X-ray tomograph.

15. The apparatus as claimed in claim 11, wherein the imaging system is a MRI device.

16. The apparatus as claimed in claim 11, wherein the imaging system is a SPECT device.

17. The apparatus as claimed in claim 11, wherein the imaging system is a PET device.

18. The apparatus as claimed in claim 11, wherein the data image signal of the body part provided is in raw form.

19. The apparatus as claimed in claim 11, wherein the data image signal of the body part provided is in a reconstructed form.

20. The apparatus as claimed in claim 11, wherein the 3-dimensional parametric description of the body part provided by the 3-dimensional parametric description generator unit is voxel-based.

* * * * *

UNITED STATES PATENT AND TRADEMARK OFFICE
CERTIFICATE OF CORRECTION

PATENT NO. : 7,636,459 B2 Page 1 of 1
APPLICATION NO. : 10/425989
DATED : December 22, 2009
INVENTOR(S) : Doré et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1028 days.

Signed and Sealed this

Ninth Day of November, 2010

David J. Kappos
*Director of the United States Patent and Trademark Office*